United States Patent
Hjärn et al.

(10) Patent No.: US 7,302,031 B2
(45) Date of Patent: Nov. 27, 2007

(54) METHOD AND ARRANGEMENT RELATING TO X-RAY IMAGING

(75) Inventors: Torbjörn Hjärn, Vaxholm (SE); Mats Danielsson, Täby (SE); Magnus Hemmendorff, Årsta (SE)

(73) Assignee: Sectra Mamea AB (SE)

( * ) Notice: Subject to any disclaimer, the term of this patent is extended or adjusted under 35 U.S.C. 154(b) by 40 days.

(21) Appl. No.: 11/259,861

(22) Filed: Oct. 27, 2005

(65) Prior Publication Data

US 2007/0098141 A1 May 3, 2007

(51) Int. Cl.
*A61B 6/04* (2006.01)
(52) U.S. Cl. ............................... 378/37; 378/23
(58) Field of Classification Search .................. 378/37, 378/21–27, 197, 195, 146–147, 4, 11, 20
See application file for complete search history.

(56) References Cited

U.S. PATENT DOCUMENTS

| | | | |
|---|---|---|---|
| 4,426,725 A | 1/1984 | Grady | |
| 5,164,976 A * | 11/1992 | Scheid et al. | 378/146 |
| 6,094,469 A | 7/2000 | Dobbs et al. | |
| 6,292,531 B1 | 9/2001 | Hsieh | |
| 6,302,579 B1 | 10/2001 | Meyer et al. | |
| 6,341,156 B1 | 1/2002 | Baetz et al. | |
| 6,411,674 B1 | 6/2002 | Oikawa | |
| 2002/0131559 A1 | 9/2002 | Launay et al. | |
| 2002/0143249 A1 | 10/2002 | Tornai et al. | |
| 2003/0058983 A1 | 3/2003 | Thayer | |
| 2003/0194051 A1 | 10/2003 | Wang et al. | |
| 2004/0141588 A1 * | 7/2004 | Francke et al. | 378/146 |
| 2004/0202280 A1 | 10/2004 | Besson | |
| 2005/0113681 A1 | 5/2005 | DeFreitas et al. | |
| 2005/0129173 A1 | 6/2005 | Eskelinen | |
| 2006/0140333 A1 | 6/2006 | Sommer | |

FOREIGN PATENT DOCUMENTS

| | | |
|---|---|---|
| WO | WO-01/60257 | 8/2001 |
| WO | WO-02/065209 | 8/2002 |
| WO | WO-03/021629 | 3/2003 |
| WO | WO-03/081220 | 10/2003 |
| WO | WO-2004/066841 | 8/2004 |
| WO | WO-2005/002443 | 1/2005 |

* cited by examiner

*Primary Examiner*—Hoon Song
(74) *Attorney, Agent, or Firm*—Lerner, David, Littenberg, Krumholz & Mentlik, LLP

(57) ABSTRACT

A novel X-ray apparatus is provided for three-dimensional imaging and in particular for tomosynthesis examination, which includes an X-ray source having a focal spot, a collimator including a plurality of slits, a detector assembly including a plurality of line detectors corresponding to respective ones of the plurality of slits and an exposure volume arranged between the collimator and the detector assembly. The X-ray source, the collimator and the detector assembly are arranged in series, so that each line detector is aligned with the corresponding collimator slit and the focal spot, and is simultaneously displaceable by a scan motion relative to the exposure volume. The scan motion is primarily a rotation around a rotation axis arranged such that the detector assembly is situated essentially between the rotation axis and the X-ray source. Combined two and three-dimensional examination are also permitted according to the disclosed methods and apparatus.

31 Claims, 6 Drawing Sheets

METHOD AND ARRANGEMENT RELATING TO X-RAY IMAGING

BACKGROUND OF THE INVENTION

The present invention relates to a method and arrangement in X-ray imaging, in particular three-dimensional imaging, and more especially tomosynthesis.

Tomosynthesis is used to create a three-dimensional picture of a person's body part, e.g. her breast, or an object, using X-rays. Currently, tomosynthesis mammography is available only for research purposes.

Tomosynthesis is essentially a limited form of Computed Tomography or CT. Normally, several projection images, e.g. 5 or 30, are acquired using a modified X-ray system with flat-panel detector and the X-ray source to tube rotated to a unique position for each projection image. Each projection image is essentially a conventional 2-dimensional digital X-ray image of the examined object. The projection images are then combined using special purpose software to produce section or "slice" images representing about a few millimeters thickness of the breast. Viewing the slices in rapid succession provides a volumetric picture of the internal structures of the breast.

Careful optimization of the acquisition process is necessary to obtain a high image quality, a fast image acquisition and keep the radiation doses low (roughly equivalent to a conventional x-ray image). In screening mammography, there are also special requirements related to ergonomics, easy positioning of patients and speed of workflow. For example, open geometry is an advantage, such that the examined object can be reached and seen from several directions. For such reasons, CT cannot substitute tomosynthesis.

EP1428473 discloses a tomosynthesis system for forming a three dimensional image of an object. The system includes an X-ray source adapted to irradiate the object with a beam of X-rays from a plurality of positions in a sector, an X-ray detector positioned relative to the X-ray source to detect X-rays transmitted through the object and a processor, which is adapted to generate a three dimensional image of the object based on X-rays detected by the detector. The detector is adapted to move relative to the object and/or the X-ray source is adapted to irradiate the object with the beam of X-rays such that the beam of X-rays follows in a non arc shaped path and/or a center of the beam of X-rays impinges essentially on the same location on the detector from different X-ray source positions in the sector.

U.S. Pat. No. 6,652,142 discloses how such an tomosynthesis system can be calibrated with respect to geometry, using a set of markers to compute the position of the X-ray source at various positions.

FIGS. 1 and 2 show prior art of a multi-slit X-ray scanner for acquisition of conventional 2-dimensional projection images for digital mammography. The patient is irradiated by a bundle of thin, X-ray beams, each of which is detected by a corresponding line detector. Each beam has a rectangular cross-section, typically 4 cm wide and 50 micrometers across. The narrow beams are created by letting the X-rays pass through a collimator 120, which is a metal plate with several narrow linear apertures, referred to as slits. For each slit, there is one corresponding line detector, which in turn is a silicon array of pixel detectors. The line detectors are arranged to scan virtually the same area of the patient, yielding redundant information and enabling noise reduction. In FIG. 1, the line detectors are mounted in a detector assembly 150. The breast to be irradiated is compressed using a compression plate 140. WO02065209, incorporated herein through reference, discloses a feature for ergonomics during positioning, i.e. the act when inserting the patient's breast. The multi-slit collimator is elevated away towards the X-ray source, hence the operator (nurse) can see and touch from a larger range of directions.

US2005008124 and WO05002443 relate to an apparatus for obtaining tomosynthesis data of an object using multi-slit scanning. Its main advantage relative to prior tomosynthesis systems, is the ability to acquire multiple projection images simultaneously. It comprises a radiation source emitting radiation centered around an axis of symmetry; a radiation detector comprising a stack of line detectors, each being directed towards the divergent radiation source to allow a ray bundle of the radiation that propagates in a respective one of a plurality of different angles to enter the line detector; an exposure area arranged in the radiation path between the divergent radiation source and the radiation detector for housing the object; and a device for moving the radiation source and the radiation detector relative the object essentially linearly in a direction essentially orthogonal to the axis of symmetry, while each of the stack of line detectors is adapted to record a plurality of line images of radiation as transmitted through the object in a respective one of the plurality of different angles.

SUMMARY OF THE INVENTION

According to an embodiment of the invention, an X-ray apparatus is provided for conducting tomosynthesis examination, which generates better and more accurate images using a low X-ray dose, and a reduced image acquisition time.

A preferred embodiment of the invention is based on multi-slit scanning and a novel non-linear rotating scan motion. In such embodiment, the main advantage relative to linear path multi-slit scanning, e.g. WO05002443, is better image quality for a given combination of detector width, distance between X-ray source and detector and a given number of scans. Due to the rotating scan motion, it is possible to obtain a substantially larger span of projection angles, i.e. the angle between rays that pass through an object point, and thus a substantially better 3D image resolution.

Alternatively, in a particular embodiment of the invention, use of a narrower detector assembly is possible. Narrow detector assemblies tend to have the following advantages:
less risks for motion blur/artifacts, thanks to shorter time between the first and last slit to pass a given object point,
a better dose curve and more well-defined image border, since a smaller part of the irradiated area does not receive radiation from all slit lines,
smaller machine and easier patient positioning,
cheaper to manufacture, its weight is lower, which in turn requires less rigid mechanics that move the detector, and thus enables a chain of lower weights and lower costs,
better suited to acquire 2D images, which is an advantage in a combo system that can acquire both 2D and 3D images,
less divergent bundle of X-ray beams, which may help reducing Heel effect and less difference between radiation for different slits.

Moreover, multi-slit scanning tend to the following advantages relative to flat-panel detectors:
parallel acquisition of multiple angles of projection images and thus substantially faster acquisition time, which implies less motion blur,
lower radiation dose, less scattered radiation,
better DQE, i.e. better photon absorption,
simple and relatively cheap manufacturing,
redundancy if many slits scan virtually the same area.

For these reasons, an X-ray apparatus for three-dimensional imaging and in particular for tomosynthesis examination is provided according to one embodiment of the invention. The apparatus comprises an X-ray source, a detector assembly, a collimator and an exposure area arranged between said collimator and said detector assembly. The collimator is a multi-slit collimator, whose output is a bundle of x-rays. The X-ray source, collimator and detector assembly are arranged in series (with respect to the X-ray path) and to be displaced relative the exposure area simultaneously and at least partly around a rotation axis. The X-ray source, collimator and detector assembly are arranged in series and rotated around a rotation axis arranged in a position such that the detector assembly is situated between said rotation axis and said x-ray source. This is opposite to mainstream computed tomography (CT) where the detector moves in an arc around the imaged object. In the invented system, the detector moves in an arc that turns away from the object. The displacement of the detector, collimator and the X-ray source will hereafter be referred to as scan motion.

Preferably, the width of the detector assembly is substantially narrower than the width of the image field. The entire image field is covered by moving the detector. A well-chosen rotation motion has the advantage that the angle of the scan arm is added to an angle between the slits of the collimator, as explained in FIG. 4 and other parts of this text. The exposure area, or volume, can have an extension from a first point to a second point. The scan motion, is a substantially continuous displacement, whereby the X-ray source is arranged to substantially continuously irradiate said exposure area from said first point to said second point. The detector assembly is arranged to receive the essentially continuous radiation and providing a processing unit with substantially continuous signals, though digitally sampled, for conversion to tomosynthesis data.

Most preferably, the scan motion and irradiation is continuous, and the scan motion is entirely around a rotation axis, and said rotation axis is on the opposite side of the detector, as seen from the X-ray source.

Preferably, the collimator includes a number of narrow apertures, also referred to as slits. The width of each slit is preferably roughly equal to the pixel size. The radiation through each aperture of the collimator produces one projection image at a time. The slit apertures are arranged with respect to the X-ray source such that multiple slits scan substantially the same object region in series, and thus multiple projection images are formed simultaneously. Each projection image has a unique angle with respect to the irradiated object. To be more specific, the angle of each beam is unique for a given point in the object, but it may vary between different points.

BRIEF DESCRIPTION OF THE DRAWINGS

In the following the invention will be described in a non-limiting way with reference to enclosed drawings, in which:

FIG. 3 is schematic illustration of a part of an x-ray apparatus, and two modes of operation, according to the present invention, where sub

FIG. 5 is an illustration of features for ergonomics of an embodiment of the present invention. In particular sub FIG. 6 is an illustration of features for ergonomics and different modes of operation of the present invention. In particular sub

DETAILED DESCRIPTION

In the following description same reference signs refer to same parts throughout the drawings.

Figures 3A, 3B:
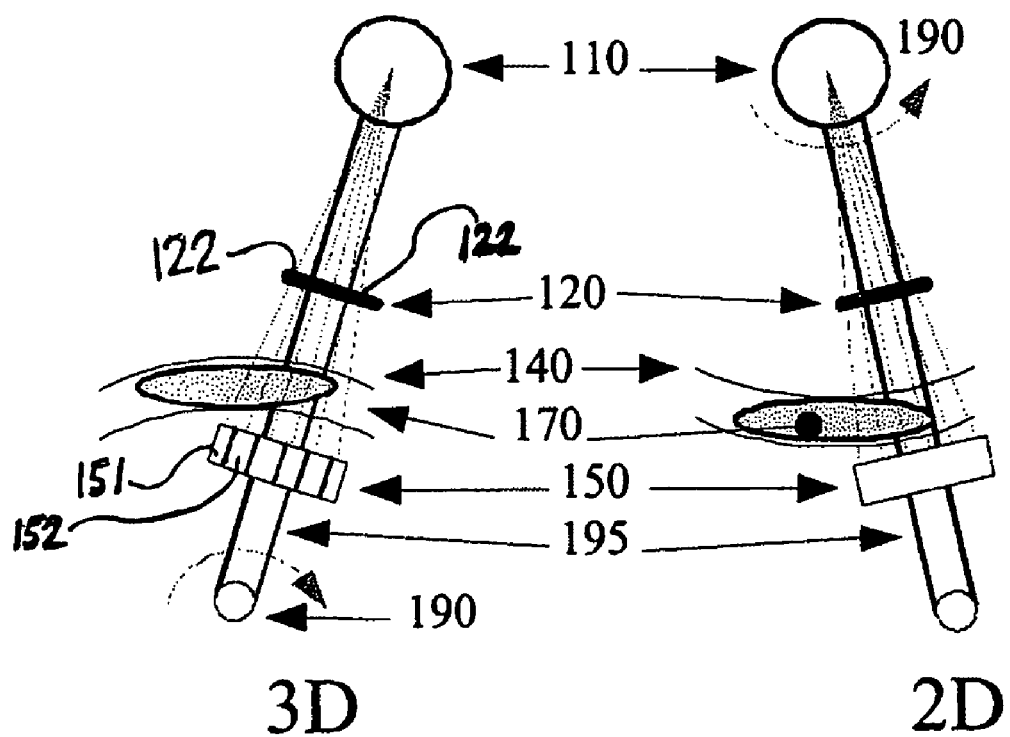
-FIGS. 3a and 3b illustrate modes for three-dimensional imaging and two-dimensional imaging respectively.

FIGS. 3a and 3b illustrate a part of an x-ray apparatus according to the invention, comprising a scan arm 195, at one end of which is mounted an x-ray source 110, spaced apart from said source a collimator 120 having a plurality of slits 122 and a detector assembly 150 having a plurality of line detectors 151, 152 etc. Compression plates are denoted with 140 and the examined object, such as a female breast, with 170.

In the embodiment of FIG. 3a, a center of rotation 190 is arranged on the other end of the scan arm 195, opposite the X-ray source 110 and below the detector assembly 150, in the opposite side of the scan arm relative to the x-ray source. Preferably, the detector assembly 150 is of the same type that can be used in a two-dimensional application. The width of the detector assembly 150 is substantially smaller than the image field, but the entire image field is covered by a scan motion. The advantage of the rotation can be understood if we study the angle of the rays that pass through one point in the object during a scan. The angle of the scan arm is added to the angle between the slits measured from the radiation source. To be more specific, the angle is the sum of the angle between the slits and the angle of the scan arm 195 (and X-ray source 110) rotation. Two beams do not hit the same point simultaneously and in the time between, the scan arm rotates some angle. A rotation axis below the examination area, in FIG. 3a, boosts the angle span and thereby enriches 3-dimensional information. The invention can be compared with an inferior alternative where the rotation axis above the examination area, which would cause a smaller projection angle due to subtraction, c.f. conventional fan beam CT. Another comparison is the already mentioned linear motion, which would neither boost nor diminish the angle. The 3D reconstruction yields better vertical resolution thanks to large span of angles of rays through the same image point.

Figure 4:
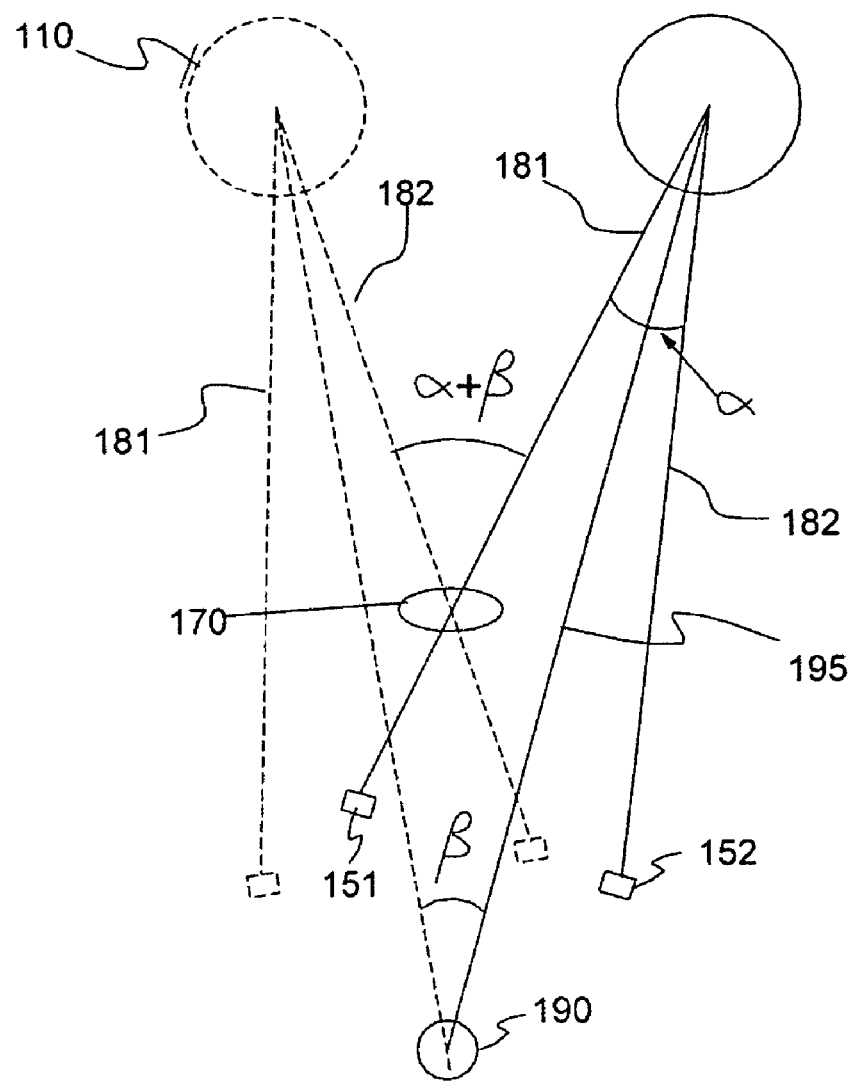
FIG. 4 is an illustration of geometric relations, in particular the projection angles, according to an embodiment of the present invention.

FIG. 4 illustrates the angle addition as mentioned in previous paragraph, i.e. the projection angles are the sum of the scan motion rotation and the angles of the slits of the collimator. 170 denotes an arbitrarily selected point object location in the examination volume, 181 and 182 denote X-ray beams through the first and the last slits of the collimator (not shown) and 151 and 152 denote corresponding line detectors. An entity, comprising the X-ray source 110, beams and detector, can be rotated around a rotation axis 190. The entity is shown in two different positions of the scan motion. In one position, the first beam 181 hits the object location 170 and in the other position, the other beam 182 hits the object location 170. Let β denote the rotation angle between said two positions. In both positions, the angle between the beams 181 and 182 is equal and, denoted α. In other words, α denotes the angle between the slits seen from the X-ray source. As the beams hit the object at different instants of time, the angle of the rotation is added to the angle of the beams. As shown in the figure, the difference of projection angles is α+β. In other words, the rotation angle is added to the angle between the slits.

A pure rotation is not the only means of obtaining angle addition. The rotation can be combined with a linear motion or motion along a curve without departing from the scope of the invention. There are many feasible alternative embodiments of the non-pure rotation, where the x-ray source rotates in direction such that projection angles are boosted. For example, the rotation axis may move or the system may slide along two linear or curved tracks, where the upper track moves faster than the lower track, or the upper track is horizontal and a point below the detector moves along a vertical track. All such solutions have in common that the entity of collimator and x-ray source move along a curve, and meanwhile the entity also rotates. The rotation is in the same direction as if the entity was rotated around the imaged object, but the speed of the rotation is slower. A pure rotation is the best choice, as all other known solutions are more expensive to produce. In addition, non-pure rotations require extra space around the detector assembly and collimator, since the direction of movement is not along the direction of their flat surface, (i.e. the collimator is essentially a thin plate, and it sweeps virtually no volume if it moves in a direction along its surface). Space is important as image quality benefits from a collimator near the imaged volume, due to the size of the focal spot of the X-ray source.

The word rotation axis is used in sense of mathematics to describe a motion, i.e. a center of rotation. Preferably, a rotation axis is implemented using mechanical parts along the rotation axis, e.g. rolling bearings, but without deviating from the scope of the invention, a rotation axis may also be implemented without any mechanical parts near the rotation axis.

As three-dimensional (3D) imaging will never fully supersede two-dimensional (2D) imaging, one aspect of the invention is a combo X-ray apparatus that can acquire both 3D and 2D images, using an extra scan motion for 2D. It would not be an alternative to acquire a full 3D image and let a computer condense the information to a 2D image, since that would mean lead to substantial loss of image quality or increased radiation dose, as lots of radiation is wasted on acquisition of 3D information and then discarded, c.f. Fourier transforms and the Fourier slice theorem.

Figure 2:
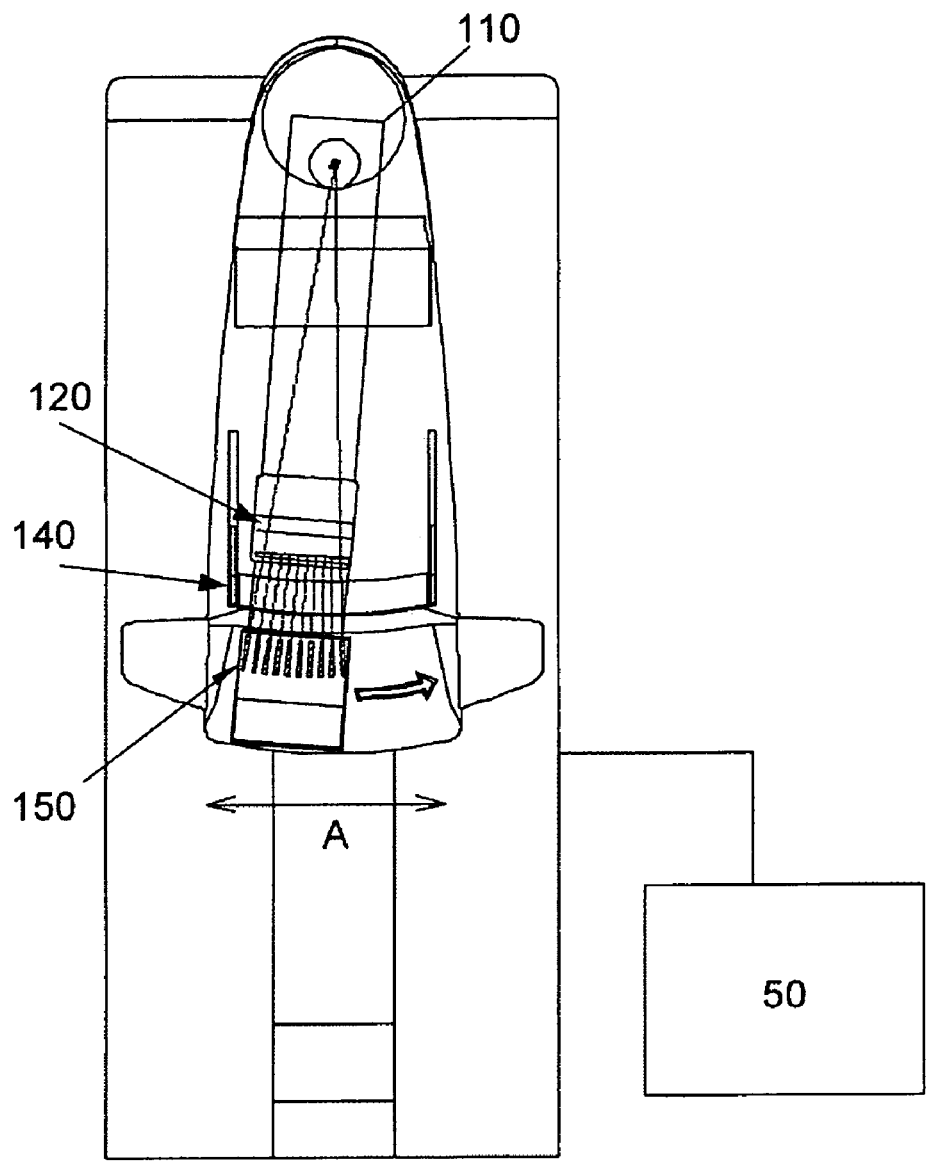

In order to offer high performance for both 2D and 3D imaging, the invention can switch between two possible centers of rotation 190 of the scan motion. FIG. 3a concerns 3D imaging, the detector should be placed as explained elsewhere in this text to obtain angle addition. FIG. 3b concerns 2D imaging, the rotation axis should be through the radiation source, just like in prior apparatus for 2D X-ray imaging in FIG. 2. When switching rotation centers, the compression plates 140 may also be switched, or turned upside down to better follow the curve of the scan motions.

Another aspect of transforming the combo apparatus from 3D mode to 2D mode is to adjust the distance from X-ray source to collimator and detector, the collimator, detector, and/or X-ray source can be adjusted along the scan arm in order to get optimal distance between detector and x-ray source for both 2D and 3D imaging. A short distance has advantages in 3D imaging, in order to obtain higher X-ray flux and larger angle between the slits. A long distance is advantageous for 2D imaging to get sharper images, and simpler patient positioning, as the present invention reduces the risk that the detector and the collimator are an obstacle for positioning the patient 170 between compression plates 140.

In one embodiment, the double rotation axes are implemented using two fixed rotation axes, where only one axis is used at a time, depending on whether 2D or 3D images are acquired. The unused axis is disconnected. The same control and driving units for the scan motion can be used in both 2D mode and 3D mode of the combo apparatus, thus lowering costs and space.

Figure 1:
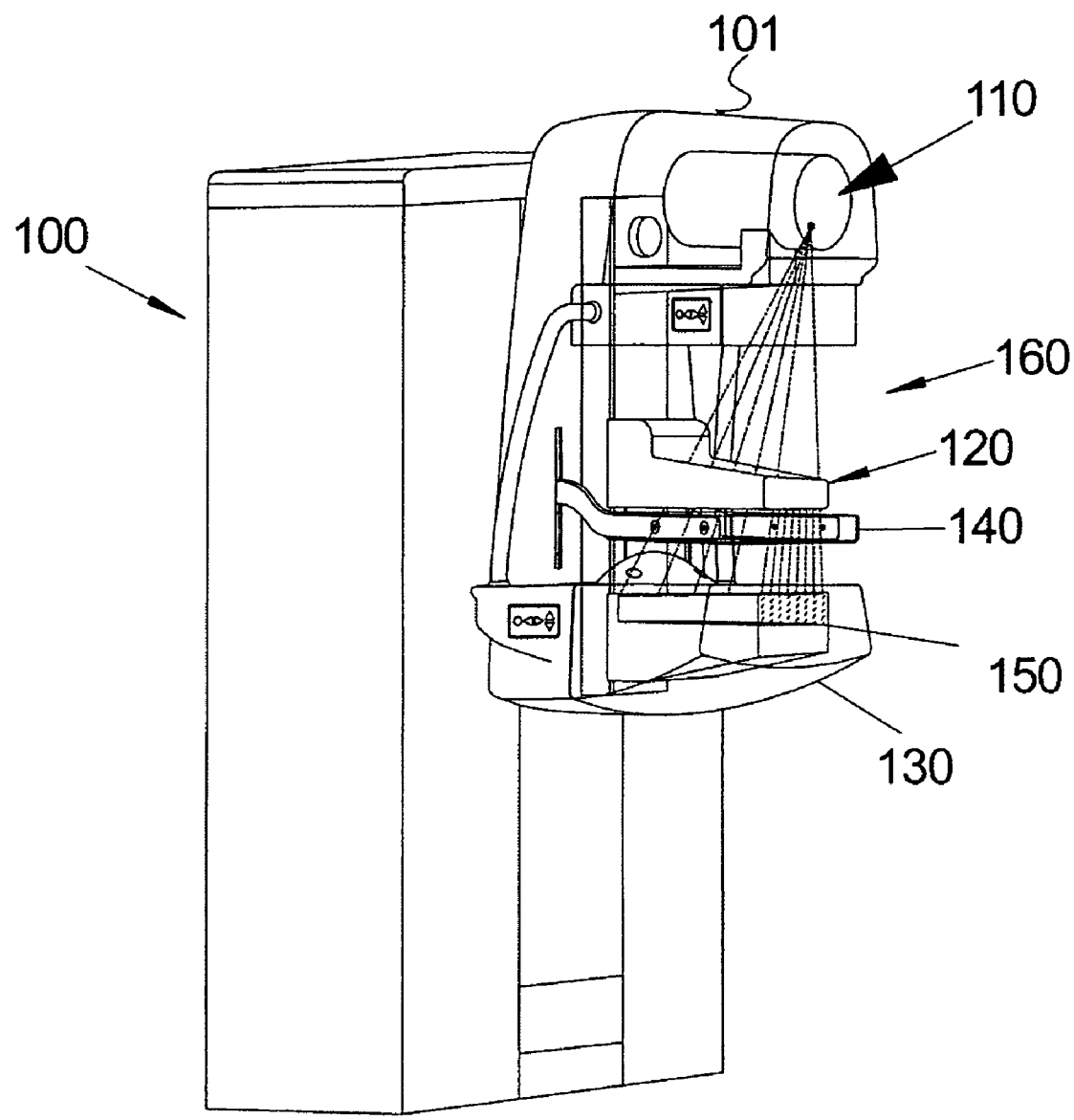
FIGS. 1 and 2 are schematic illustrations of an x-ray arrangement according to the prior art.

Just like the prior 2D slit scanning system (FIG. 1 and FIG. 2), the novel 3D tomosynthesis scanner needs to be calibrated. Calibration is essentially a set of measurements, which will be used for corrections that will be applied in software during image reconstruction. The following calibrations should be performed:

scanner geometry, with respect to distance between collimator slits and relative positioning of detector lines, measured in the pixel domain and the position of the rotation axis, gray-level of each individual channel in each detector line, which partly depends on thresholds of photon energies and width of collimator slits.

The gray-level should be calibrated for a set of different thickness of the irradiated object or patient breast. One reason is to correct for beam hardening, i.e. the intensity of a non-monochromatic X-ray beam through a homogenous object does not drop off according to a perfect exponential curve with respect to the object thickness, due to a mixed spectrum of X-ray photon energies. Beam hardening is a problem for 3D reconstruction algorithms that assume that the logarithm of the detected intensity is linear with respect to the thickness of a homogenous object. Therefore, gray-levels may be mapped to a perfect exponential curve with respect to thickness, but any known curve will do for intermediate results. In the preferred embodiment, the curve is essentially logarithm, which makes the intensity of the corrected image linear with respect to object thickness, and therefore justifies linear interpolation of calibration data.

When the novel multi-slit scanner runs in 2D mode, i.e. with rotation around the X-ray source, most calibration can be carried out according to prior art. Prior 2D routines can be used to calibrate gray-level and position of line detector and slits. After switching to 3D mode, the rotation axis can be calibrated by scanning a known, or partially know, object and finding its corresponding relative coordinates in each of the projection images, either by finding coordinates of edges or using any algorithm of image registration. Long edges tend to comprise more statistics than small markers, but a single edge can only be used to measure positions in one direction, perpendicular to the edge. Therefore multiple edges of different orientation should be combined. A number of equations, based on basic geometry relations, arise and those equations are solved. For best accuracy, a lot more equations than unknowns are used, and the over-determined equation systems are solved in least squares sense.

The calibration is more sophisticated when calibrating without help from the 2D-mode. We have to calibrate using only a scan motion that is not through the X-ray source. There are many more unknowns in the equations that arise when matching projection images of known or partially known objects. The extra unknowns are many: gray-level of each detector channel and relative position of detector lines and slits. Either a computer processes heavy numerical optimization algorithm or a series of special phantoms are used, which make it possible to calibrate some parameters without dependence of other parameters. Gray-level calibration can be simplified by using a set of long cylindrical phantoms made of PMMA or other plastics that are inserted perpendicularly to the X-rays, whereby all projection images will get the same gray-level profile thanks to the circular cross-section. The gray-level profile is independent of incident angle under assumption that the cylinder is inserted perpendicular to the rays, and thus all projection images will get the same gray-level. We neglect the fact that a straight cylinder cannot be perpendicular to rays in the front and rear of the examination area, since a smooth variation of gray-level perpendicular to the scan direction does not impair image quality. Such variations can also be taken into account if the cylinder is inserted with a slight accuracy. Another possibility is to use PMMA plates of different thickness and find the peak intensity where X-rays pass perpendicularly through the plate, which is where the incident ray is orthogonal to the plate.

The edges of PMMA cylinders can also be used to calibrate distance between collimator slits and rotation center. To obtain equations for the detector positions along the slits, we need to scan and extra phantom with edges that are parallel to the scan direction, or at least not perpendicular to the scan direction.

In a typical embodiment, there is a trade-off when choosing the distance between the rotation centre and the examination area. A small radius gives high effect for the angle span, but a short radius causes several drawbacks, such as a curved image field. Very narrow detectors cause increased scatter, (though the scatter is still very low compared to flat-panel detectors and conventional film-screen mammography). In a typical embodiment of the invention, depending on application, the geometry is chosen so that projection angles are doubled or tripled relative to the angles between the slits.

For ergonomics reasons and the act of patient 170 positioning, two different embodiments of the invention allows imaging parts to moved further away from the patient during the act of positioning, i.e. putting the patient's breast in a proper position. The operator of the apparatus can see and touch from different angles while positioning the patient. Moving the collimator is already disclosed, as mentioned earlier, but moving the detector is an aspect of the present invention, where the scan arm 195 extends beyond the detector and there are advantages from being turned upside down, such that the detector is above the patient's breast.

FIGS. 6a-6d show an embodiment where the collimator and detector can be moved along the scan arm 195. One reason is to use a more divergent bundle of X-rays beams for 3D than for 2D. The most important is, however, ergonomics and ease of positioning the patient or object to irradiate 170 between the compression plates 140. Many clinics or examinations sites have a very fast workflow for 2D mammography and it is important that the collimator or the detector is not an obstacle for the hands of a nurse when positioning a patient's breast. Experience also shows that a low X-ray tube can be obstacle for the patient's head in 2D imaging.

Figures 6A, 6B, 6C, 6D:
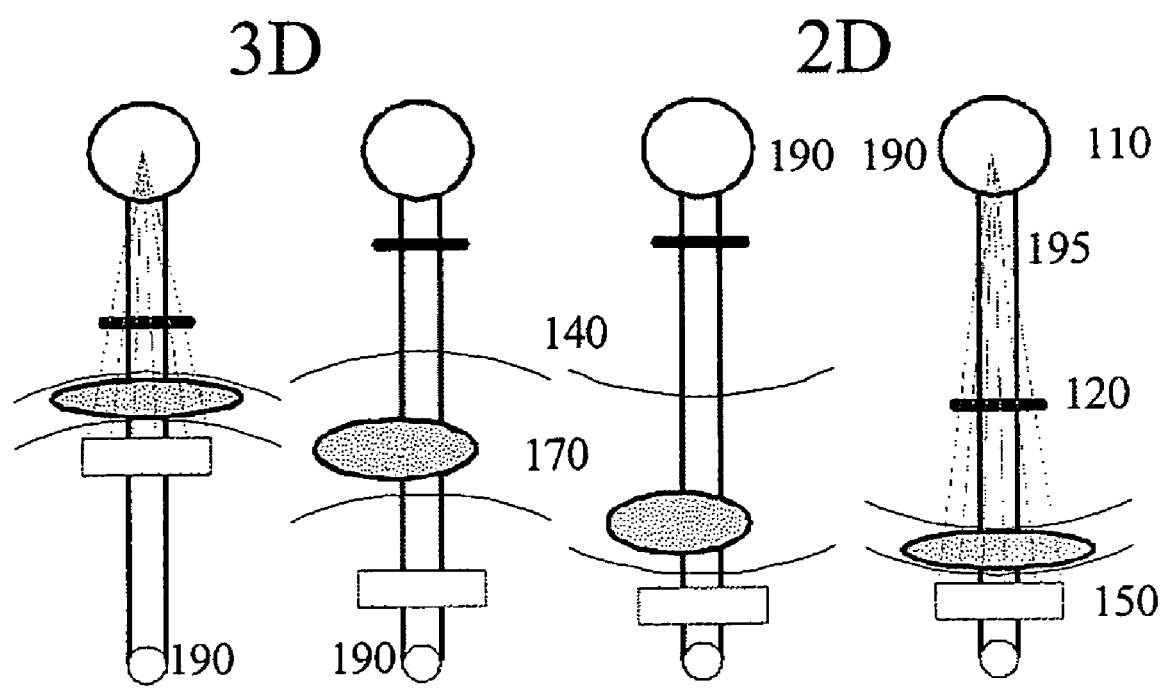
-FIGS. 6a and 6b illustrate a three-dimensional imaging mode during the states of irradiation and preparation respectively, and sub
-FIGS. 6c and 6d illustrate a two-dimensional imaging mode during the states of preparation and irradiation respectively.

FIG. 6a shows the position during acquisition of 3D images. FIG. 6b shows that the collimator and detector can be moved away positions when preparing for 3D acquisition. FIG. 6c shows that the same positions can be used when preparing for a 2D acquisition, except that the compression plates are curved around the rotation center for 2D. FIG. 6d shows that the collimator is lowered during acquisition of 2D images.

Figure 5A:
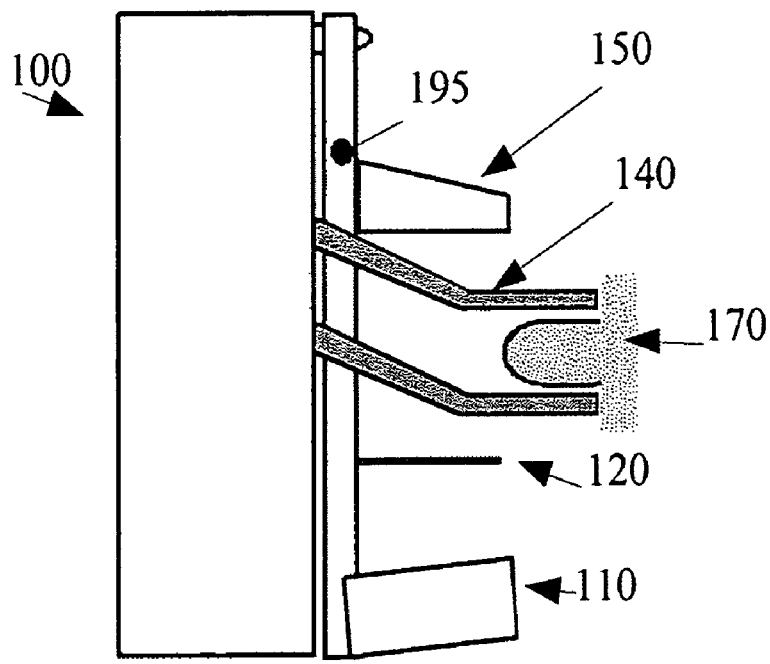
-FIG. 5a illustrates the apparatus in a state for preparation, and sub
Figure 5B:
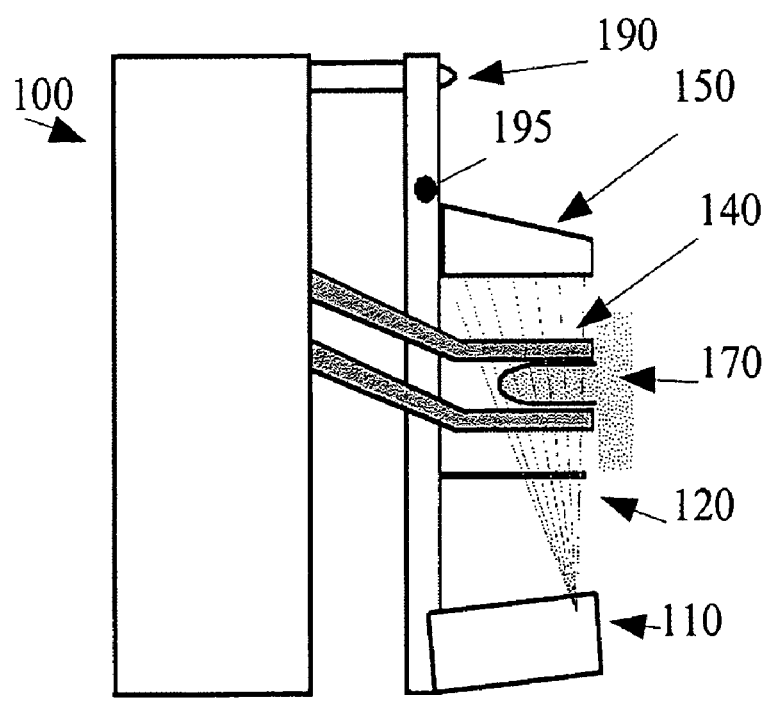
-FIG. 5b illustrates the apparatus in state during irradiation.

For ergonomic reasons, the x-ray apparatus can be arranged upside down or in any other angle. FIGS. 5a and 5b show schematically the x-ray apparatus 100 arranged having its x-ray source 110 radiating from a position beneath the examination area, instead of from above as in mainstream 2D mammography systems. This embodiment has advantages with respect to ergonomics and positioning of the patient. The patient's head is far from the X-ray tube and the image field is curved in opposite direction relative to the patient's breast. In conventional 2D mammography, it is common to acquire images with the gantry tilted 45-60 degrees, and some 2D systems turns automatically by a computer, based on type of examination. Just like prior art 2D systems, the preferred embodiment of the invented 3D system may turn automatically to a pre-defined angle, based on the type of examination to be performed, according to an internal or external computer system.

FIG. 5b also shows another implementation of easy position for 3D imaging. The detector 150, collimator 120 and tube 110 can be pulled away from the patient meanwhile positioning for a 3D examination. FIG. 5b suggests that an entity comprising the scan arm, detector, collimator and tube is pulled away along a linear track. In another embodiment, the entity is rotated away around a rotation axis. The compression plates 140 are not moved, as they are needed for positioning the patient.

In a typical embodiment, a computer, arranged externally or internally, may be used for reconstructing the 3D image. The computer can be a combination of a conventional computer and possibly special computational hardware running image construction algorithms. Among well-known algorithms are filtered back-projection with specially designed filters, iterative algorithms such as, EM, least squares and ML optimizations, proposed by Lange and Fessler.

This invention is not limited to a one-scan machine. It is possible to make two or more scans to obtain double or multiple number of projection images.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. An X-ray apparatus for three dimensional imaging and in particular for tomosynthesis examination, comprising an X-ray source having a focal spot, a collimator including a plurality of slits, a detector assembly including a plurality of line detectors corresponding to respective ones of said plurality of slits and an exposure volume arranged between said collimator and said detector assembly, said X-ray source, said collimator and said detector assembly being arranged in series, so that each said line detector is aligned with said corresponding collimator slit and the focal spot, and simultaneously displaceable by a scan motion relative to said exposure volume, wherein said scan motion is primarily a rotation around a rotation axis arranged such that said detector assembly is situated essentially between said rotation axis and said X-ray source.

2. The X-ray apparatus according to claim 1, wherein an interval of projection angles through a location in said exposure volume is substantially larger than an interval of angles of said corresponding collimator slits from a point of view of said X-ray source.

3. The X-ray apparatus according to claim 2, wherein said scan motion is a pure rotation around said rotation axis.

4. The X-ray apparatus according to claim 3, further comprising an additional center of rotation of said scan motion, arranged through said X-ray source, said apparatus being operable to use said additional center of rotation to acquire two-dimensional images.

5. The X-ray apparatus according to claim 1, wherein said detector assembly is displaceable away from said exposure volume, at one or more times being at least one of prior to or during positioning of a patient or after irradiation of the patient.

6. The X-ray apparatus according to claim 5, wherein said detector assembly, said collimator and said X-ray source are mounted on a common entity moveable rigidly and essentially horizontally in a direction away from an object held in said exposure volume.

7. The X-ray apparatus according to claim 5, wherein said detector assembly, said collimator and said X-ray source are mounted on a common entity moveable away from an object held in said exposure volume by rotation around at least one rotation axis.

8. The X-ray apparatus according to claim 5, wherein said detector assembly and said collimator are mounted on a common scan arm, and said detector assembly is displaceable along said scan arm in a direction away from said exposure volume.

9. A method of producing a three-dimensional image in an X-ray apparatus including an X-ray source, a detector assembly including a plurality of line detectors, a collimator including a plurality of slits corresponding to respective ones of said plurality of line detectors, and an exposure volume arranged between said collimator and said detector assembly, said X-ray source, said collimator and said detector assembly being arranged in series and being displaceable relative to said exposure volume simultaneously and around a common rotation axis, said exposure volume having an extension from a first point to a second point, wherein said method comprises the steps of rotating said X-ray source, said collimator and said detector assembly arranged in series around said rotation axis to a first position such that said detector assembly is situated between said rotation axis and said X-ray source.

10. The method of claim 9, wherein an interval of projection angles is substantially larger than an interval of angles between said corresponding slits of said collimator from a point of view of said X-ray source.

11. The method of claim 9, further comprising a step of moving said detector assembly away from said exposure volume prior to inserting a body part of a patient to be irradiated, whereby said body part is accessible from a larger range of directions, and after positioning of said body part, said detector assembly is moved back to a position for irradiation of said exposure volume.

12. The method of claim 9, wherein said detector assembly is moved away from said exposure volume in a direction along a scan arm on which said collimator and said detector assembly are mounted.

13. An X-ray apparatus for acquisition of both two-dimensional and three-dimensional images, comprising an X-ray source having a focal spot, a collimator including a plurality of slits, a detector assembly having a plurality of line detectors corresponding to respective ones of said plurality of slits, and an exposure volume arranged between said collimator and said detector assembly, said X-ray source, said collimator and said detector assembly being arranged in series, so that each said line detector is aligned with said corresponding slit of said collimator and the focal spot, and being simultaneously displaceable relative to said exposure volume in order to acquire image data for each location in said exposure volume, wherein said X-ray source, said collimator and said detector assembly are displaceable through a scan motion, said scan motion including a rotation around a rotation axis during irradiation of said exposure volume, and said rotation axis is moveable between at least a first position and a second position, wherein said first position is through the focal spot of said X-ray source and said second position is arranged such that said detector assembly is situated essentially between said rotation axis and said X-ray source providing different projection angles.

14. The X-ray apparatus according to claim 13, wherein said first position of said rotation axis through said X-ray source is usable for acquisition of two-dimensional images, and said second position of said rotation axis is usable for acquisition of three-dimensional images.

15. The X-ray apparatus according to claim 14, wherein one effect in acquisition of three-dimensional images is that an interval of angles of different X-ray beams through a location in said exposure volume is substantially larger than an angle between said slits of said collimator from said X-ray source.

16. The X-ray apparatus according to claim 15, wherein a distance from said detector assembly to said X-ray source is variable during irradiation of said exposure volume between a first distance and at least a second distance such that the change of said distance substantially increases or decreases an angle between said slits of said collimator seen from said X-ray source.

17. The X-ray apparatus according to claim 15, comprising means for calibration operable to calibrate gray-levels using images first acquired using a scan motion which is a pure rotation around said rotation axis through said X-ray source.

18. The X-ray apparatus according to claim 17, wherein said means for calibration is operable to calibrate a sensitivity of said detector assembly and an acquisition geometry by scanning one or more known objects and solving calibration coefficients from equations that arise from relations of measured data in accordance with at least one of geometry and an attenuation of radiation from said X-ray source.

19. The X-ray apparatus according to claim 15, wherein said detector assembly is mounted on a scan arm moveable in a direction away from a patient along said scan arm during or prior to preparation for irradiation.

20. The X-ray apparatus according to claim 15, wherein said detector assembly, said collimator and said X-ray source are mounted on a common entity moveable away from a patient prior to positioning of the patient, said entity being moveable again toward the patient prior to irradiation.

21. An X-ray apparatus for three dimensional imaging and in particular for tomosynthesis examination, comprising an X-ray source having a focal spot, a collimator including a plurality of slits, a detector assembly including a plurality of line detectors corresponding to respective ones of said plurality of slits and part operable to hold at least one of an object or a body part of a patient, said holding part being disposed between said collimator and said detector assembly, said X-ray source, said collimator and said detector assembly being arranged in series, so that each said line detector is aligned with said corresponding slit of said collimator and the focal spot and are simultaneously displaceable relative to the at least one of an object or body part in order to acquire image data for locations in at the least one of an object or body part at different projection angles, wherein said detector assembly is moveable away from said holding part when the X-ray apparatus is not irradiating the at least one of an object or body part of the patient.

22. The X-ray apparatus according to claim 21, wherein said detector assembly is moveable away from said holding part while preparing the at least one of the object or body part for irradiation and said detector assembly is moveable towards said holding part immediately prior to the irradiation.

23. The X-ray apparatus as claimed in claim 21 further comprising a scan arm, wherein said X-ray source, said collimator and said detector assembly are mounted to said scan arm and said scan arm is moveable away from said holding part when the X-ray apparatus is not irradiating the at least one of an object or body part.

24. The X-ray apparatus as claimed in claim 23, wherein said scan arm is moveable in a linear direction away from said holding part.

25. The X-ray apparatus as claimed in claim 24, wherein said scan arm is rotatable around a rotation axis away from said holding part.

26. The X-ray apparatus as claimed in claim 23, wherein said detector assembly is moveable in a linear direction along a length of said scan arm away from at least a portion of said holding part.

27. The X-ray apparatus as claimed in claim 21, wherein said holding part includes compression plates.

28. The X-ray apparatus for acquisition of both two-dimensional and two-dimensional mammography images, comprising an X-ray source having a focal spot, a collimator including a plurality of slits, a detector assembly including a plurality of line detectors corresponding to respective ones of said plurality of slits, and a part operable to hold at least one of an object or a body part of a patient disposed between said collimator and said detector assembly, said X-ray source, said collimator and said detector assembly being arranged in series, so that each said line detector is aligned with said corresponding slit of said collimator and the focal spot, and is simultaneously displaceable relative to said at least one of the object or body part in order to acquire image data for locations in the at least one of an object or body part, wherein said X-ray source, said collimator and said detector assembly are displaceable by a scan motion during irradiation of said at least one of an object or body part, and said scan motion for acquisition of two-dimensional images is a rotation around a rotation axis through said X-ray source, and during preparation for a three-dimensional scan, said detector assembly is moveable to a position for preparation, said position for preparation being a position other than a position of said detector assembly usable during irradiation, whereby an operator of the X-ray apparatus can see and touch the at least one of an object or a body part held by said holding part from a larger range of directions when said detector assembly is in said position for preparation.

29. The X-ray apparatus according to claim 28, wherein said collimator, said detector assembly and said X-ray source are mounted on a common rigid entity moveable horizontally away from said holding part to said position for preparation.

30. The X-ray apparatus according to claim 28, further comprising a scan arm, wherein said collimator, said detector assembly and said X-ray source are mounted to said scan arm, and said detector assembly is moveable along said scan arm in a direction relative to at least a portion of said holding part to said position for preparation.

31. The X-ray apparatus as claim in claim 28, wherein said holding part includes compression plates.

* * * * *

UNITED STATES PATENT AND TRADEMARK OFFICE
CERTIFICATE OF CORRECTION

| | | |
|---|---|---|
| PATENT NO. | : 7,302,031 B2 | Page 1 of 1 |
| APPLICATION NO. | : 11/259861 | |
| DATED | : November 27, 2007 | |
| INVENTOR(S) | : Torbjoern Hjarn, Mats Danielsson and Magnus Hemmendorff | |

It is certified that error appears in the above-identified patent and that said Letters Patent is hereby corrected as shown below:

Column 1, line 36 "three dimensional" should read --three-dimensional--.
Column 1, line 41 "three dimensional" should read --three-dimensional--.
Column 1, line 49 "an" should read --a--.
Column 2, line 10 after "systems" delete ",".
Column 2, line 62 "tend" should read --tends--.
Column 3, line 33 after "motion" delete ",".
Column 3, line 38 "providing" should read --provide--.
Column 3, line 41 "is" should read --are--.
Column 4, line 51 after "axis" insert --is--.
Column 5, line 49 after "would" delete "mean".
Column 6, line 30 "thickness" should read --thicknesses--.
Column 6, line 50 "know" should read --known--.
Column 7, line 4 "make" should read --makes--.
Column 7, line 26 "and" should read --an--.
Column 7, line 41 "allows" should read --allow--.
Column 7, line 42 before "moved" insert --be--.
Column 7, line 62 before "obstacle" insert --an--.
Column 7, line 65 "positions" should read --in position--.
Column 8, line 15 "turns" should read --turn--.
Column 8, line 23 after "patient" insert --,--.
Column 8, line 51 "three dimensional" should read --three-dimensional--.
Column 10, line 57 "three dimensional" should read --three-dimensional--.
Column 11, line 3 before "at" insert --the--.
Column 11, line 33 "two-dimensional" should read --three-dimensional--.
Column 12, line 34 "claim" should read --claimed--.

Signed and Sealed this

Twenty-fourth Day of March, 2009

JOHN DOLL
*Acting Director of the United States Patent and Trademark Office*